(12) United States Patent
Berndt

(10) Patent No.: US 6,826,949 B1
(45) Date of Patent: Dec. 7, 2004

(54) METHOD AND APPARATUS FOR GUIDING A LIQUID SAMPLE TOWARDS A SENSING SURFACE

(75) Inventor: Klaus W. Berndt, Timonium, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 10/461,263

(22) Filed: Jun. 13, 2003

(51) Int. Cl.$^7$ .......................... G01N 1/00; G01N 33/00; B01L 3/00; B01L 9/00
(52) U.S. Cl. ................. 73/64.56; 73/32 A; 73/61.41; 73/61.49; 73/61.75; 73/61.79; 73/863.21; 73/864.91; 422/102; 422/104
(58) Field of Search .................. 73/24.01, 32 A, 73/61.41, 61.45, 61.49, 61.79, 61.75, 863, 863.21, 863.22, 863.41, 863.42, 863.43, 864.91, 863.51, 863.52, 863.53, 863.54, 64.56; 422/68.1, 82.01, 82.02, 99, 101, 102, 104

(56) References Cited

U.S. PATENT DOCUMENTS

| | | | | |
|---|---|---|---|---|
| 3,238,452 A | * | 3/1966 | Schmitt et al. ............. 324/666 |
| 3,583,627 A | * | 6/1971 | Wilson ......................... 494/36 |
| 3,983,743 A | * | 10/1976 | Olin et al. .................. 73/28.06 |
| 4,242,096 A | * | 12/1980 | Oliveira et al. .............. 436/500 |
| 4,387,603 A | * | 6/1983 | Nelson ..................... 73/863.22 |
| 4,789,804 A | * | 12/1988 | Karube et al. .............. 310/311 |
| 4,848,139 A | * | 7/1989 | Blake-Coleman et al. . 73/61.75 |
| 5,076,933 A | * | 12/1991 | Glenn et al. ................. 210/641 |
| 5,455,475 A | * | 10/1995 | Josse et al. ............ 310/316.01 |
| 5,641,895 A | * | 6/1997 | Grant ......................... 73/64.56 |
| 5,747,671 A | * | 5/1998 | Hirota et al. .............. 73/61.75 |
| 6,101,886 A | * | 8/2000 | Brenizer et al. ......... 73/863.23 |

OTHER PUBLICATIONS

Rickert et al. "A new affinity biosensor: Self-assembled thiols as selective monolayer coatings of quartz crystal microbalances", Biosensors and Bioelectronics, vol. 11, No. 6/7, 1996 no month, pp. 591–598.*

* cited by examiner

Primary Examiner—Michael Cygan
(74) Attorney, Agent, or Firm—Bruce S. Weintraub, Esq.

(57) ABSTRACT

A liquid sample sensing device comprises a set of stackable liquid sample base units that are adapted to be stacked together to form multiple sample volumes that are substantially sealed, each with an electroacoustic member disposed therein having a surface adapted for binding to a particular target molecule. Top and bottom units are preferably attached to a closed loop of flexible tubing and a peristaltic pump. Individual electroacoustic members in the stack can each be adapted to bind with different target molecules, allowing for a multiple target assay. Alternately, a plurality of electroacoustic members can be adapted to bind with the same type of target molecule, thereby increasing the sensitivity of the sensing device. The base units are adapted such that sample liquid is caused to flow over and be in close proximity to the sensing surface of each electroacoustic member as the sample liquid flows from one base unit to the next, thereby increasing the efficiency of binding.

22 Claims, 7 Drawing Sheets

1

METHOD AND APPARATUS FOR GUIDING A LIQUID SAMPLE TOWARDS A SENSING SURFACE

FIELD OF THE INVENTION

The present invention relates to the detection and identification of infectious diseases. Specifically, the present invention relates to a method and apparatus for the detection of disease-causing particles such as bacteria, viruses and other particulate entities in liquid samples with extremely high sensitivity.

BACKGROUND OF THE INVENTION

Quartz crystal microbalances ("QCM") have been developed as sensitive chemical and biochemical sensing devices and can be used for the detection of disease-related particles such as viruses and bacteria in liquid samples (see e.g. Thompson, M. et al., Analyst Vol. 116, pp. 881–890, 1991; Rickert, J. et al, Biosensors & Bioelectronics Vol. 12, pp. 567–575, 1997; Uttenthaler, E. et al., Biosensors & Bioelectronics 16, 735–743, 2001). In this technology, a binding partner such as an antibody is attached to the surface of a small resonant quartz crystal with a mechanical resonance frequency typically in the 10 to 30 MHz region. If a disease-related particle binds to the antibody, the resonance frequency of the quartz crystal shows a very small shift, whereby such shift in frequency or a correlated phase shift between the electrical excitation and the mechanical vibration is an indication that an antibody-specific binding partner was present in the liquid sample.

A significant improvement in the detection sensitivity of a QCM biosensor has been achieved by applying the technology of rupture event scanning ("REVS"), (see Dultsev, F. N. et al., Langmuir Vol. 16, 5036–5040, 2000; Cooper, M. A. et al., Nature Biotechnology Vol. 19, 833–837, 2001; WO 01/02857 A1 to Klenerman et al.). In the REVS technology, as in the classic QCM technology, a binding partner such as an antibody is attached to the surface of a small resonant quartz crystal with a mechanical resonance frequency typically in the 10 to 20 MHz region. The liquid sample containing bacteria or viruses is brought into contact with the activated crystal surface so that binding events can take place.

After a 30-minute incubation period, the resonant quartz crystal is operated as close as possible to the fundamental mechanical resonance frequency, whereby the driving power for the quartz crystal is monotonously increased, until suddenly the binding between the binding partners is broken up. According to the inventors of REVS, the breaking or "rupture" event can be detected due to the emission of noisy sound waves with a preferred frequency spectrum around the third harmonic of the fundamental resonance frequency. The quartz crystal acts as a sensitive microphone, and the generated electrical signal is monitored via an electric resonance circuit tuned to a frequency close to the third harmonic of the fundamental resonance frequency of the crystal. The REVS technology has the potential of detecting the breaking-away of only a few binding partners, thereby enabling extremely sensitive detection.

As mentioned above, a certain incubation time is required to bring the targets such as bacteria or viruses that are present within the liquid sample into contact with the activated crystal surface, so that binding events can take place. Movement of the targets usually takes place due to diffusion. The time, t, needed for a target to cross over a distance, d, via diffusion is given by the equation $t=d^2/2D$, where D is the so-called diffusion coefficient. Assuming a typical diffusion coefficient $D=7*10$ $Cm^2/s$ for a large molecule, such target would need two hours to cross over a distance of 1 mm. Even larger distances may be required if the sample volume cannot be extremely small, which is often the case for medical samples having a low target concentration.

One could try to resolve this problem by pre-concentrating the target molecules via centrifugation or similar process steps, but this requires significant extra effort and makes the detection more time-consuming and more expensive. One goal of the present invention is, therefore, to avoid the need for a pre-concentration step. Other goals of the invention are to allow for the handling of large sample volumes, and to allow for multiplexed detection within one detection device.

SUMMARY OF THE INVENTION

The present invention is related to diagnostic sensing devices where a liquid sample has to come in contact with a sensing surface, or with a plurality of sensing surfaces. The invention is in particular of interest for sensing devices where the sample liquid contains the target molecules that have to be detected in low concentration, and where, therefore, a large sample volume has to be processed to achieve detection at all. The present invention avoids the need for a pre-concentration step, and also allows for the handling of large sample volumes, and to further increase sensitivity through multiplexed detection within one detection device.

BRIEF DESCRIPTION OF THE DRAWINGS

The invention will be more readily understood with reference to the embodiments illustrated in the attached drawing figures, in which.

In the drawing figures, it will be understood that like numerals refer to like features and structures.

DETAILED DESCRIPTION OF THE PREFERRED EMBODIMENTS

Figure 1A:
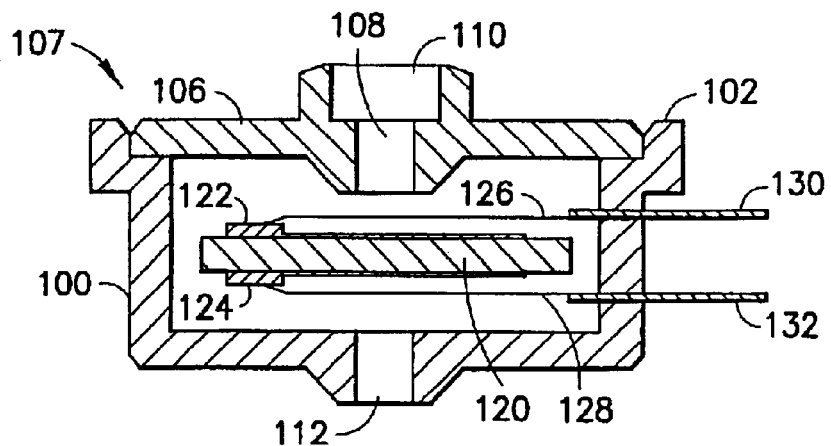
FIG. 1(a) shows a top unit that is employed in a detection apparatus according to an embodiment of the present invention.
Figure 1B:
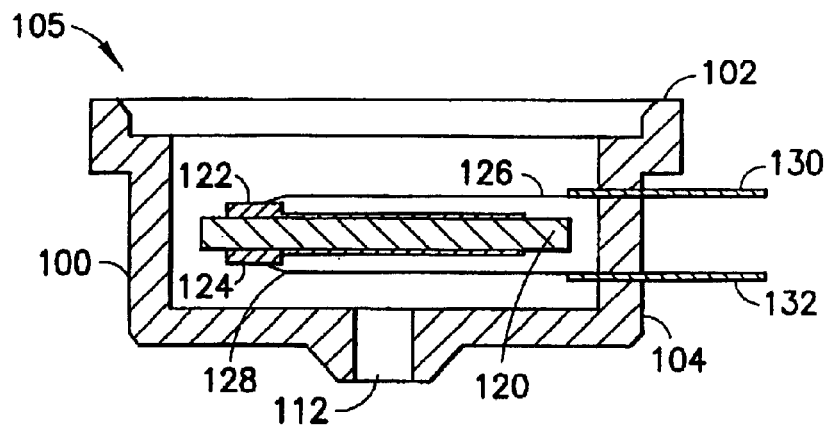
FIG. 1(b) shows a base unit that is employed in a detection apparatus according to an embodiment of the present invention.

The preferred embodiments of the invention will now be described with reference to the attached drawing figures. An apparatus according to the present invention comprises in its simplest form a base unit as shown in FIG. 1(b). The base unit contains a housing 100 that has features allowing the stacking of such base units. One of said features has the form of flange 102, whereby the inner opening of flange 102 has a diameter that is identical to the outer diameter of housing 100 on its opposite end 104. Due to the presence of flange 102 in a first base unit, a second base unit can be attached to the first base unit with the opposite end 104 of the second base unit. By repeating this operation, a stack of base units 105 as shown in FIG. 2 can be built.

Figure 1C:
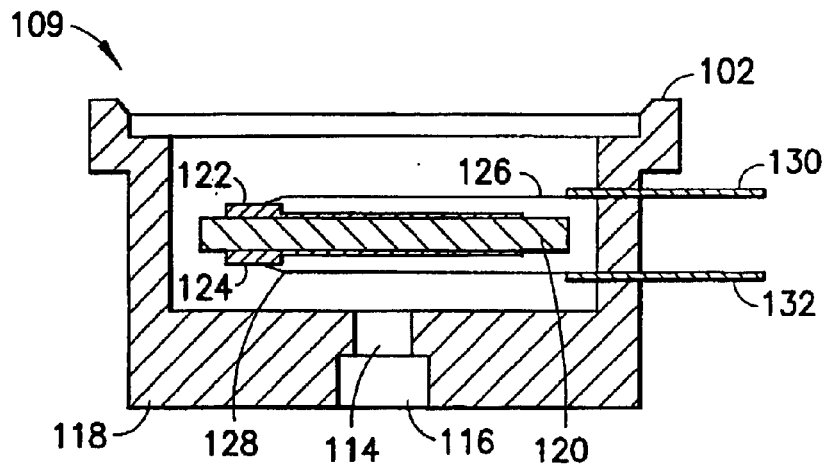
FIG. 1(c) shows a bottom unit that is employed in a detection apparatus according to the present invention.
Figure 2:
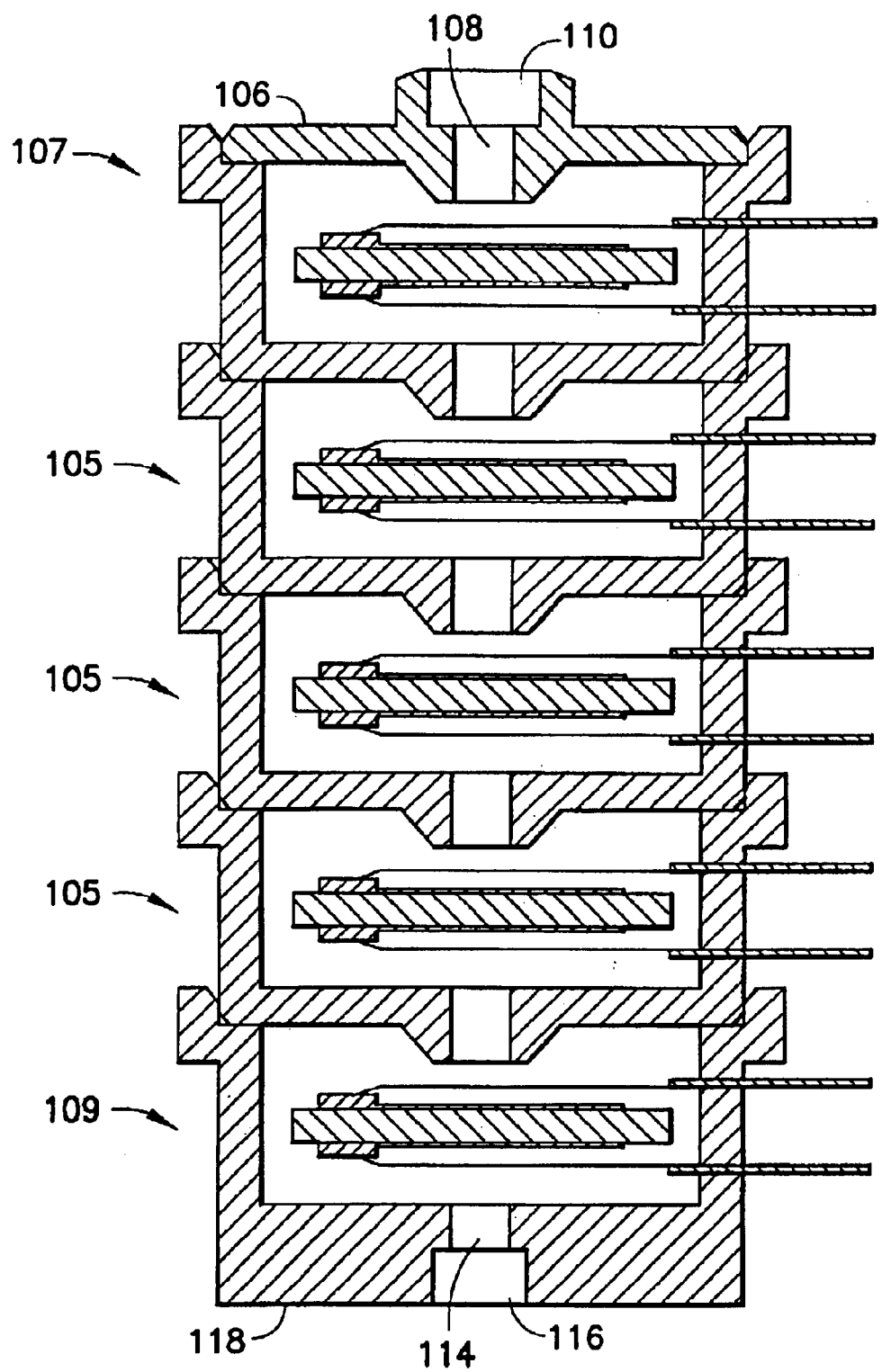
FIG. 2 illustrates a stack of base units, with a top unit at the top, and a bottom unit at the bottom according to an embodiment of the present invention.

A stack of base units as shown in FIG. 2 preferably contains identical base units, except for the top unit 107 and the bottom unit 109. FIG. 1(a) shows a top unit 107 in more detail, while FIG. 1(c) shows a bottom unit 109 in more detail. In contrast to a base unit 105, a top unit 107 has a lid 106 attached to flange 102. Lid 106 contains an opening 108 for receiving sample fluid, and a second flange 110 allowing attaching a fluid conduit such as flexible tubing. While a base unit 105 comprises a simple through hole 112 in its lower end 104, a bottom unit 109 contains a through hole 114 and a third flange 116 in its lower end 118, also allowing attaching a fluid conduit such as flexible tubing.

As indicated in FIGS. 1(a), 1(b), and 1(c), base units 105, top units 107, and bottom units 109 each contain a body 120 with a sensing surface, whereby the sensing surface has preferably been prepared to allow for specific binding of target molecules. In the example of FIG. 1, body 120 represents a piezo-acoustic crystal that can be brought into mechanical vibration by means of an electrical RF excitation. For that purpose, crystal 120 contains electrodes 122 and 124, and crystal 120 is mounted within a unit by means of two support wires 126 and 128 that serve also as electrical conductors for bringing the RF field to the crystal, and picking up an electrical detection signal from the crystal. Support wires 126 and 128 are preferably connected to feed-throughs 130 and 132 that extend through a unit's housing 100 to the outside of the unit.

It should be understood by those of ordinary skill in the art, that body 120 is presently contemplated to embody the best mode of the invention as an electro-acoustic body such as a piezo-electric device. However, a broad range of sensing bodies are considered to be within the scope of the present invention, including bodies with surfaces prepared for binding to specific target molecules, as well as bodies with surface not intended for binding. Furthermore, sensing bodies that generate a sensor output signal based on changes in the bodies' electrical conductivity, and electrochemical sensing bodies are specifically considered to be within the scope of the present invention. Other types of sensing bodies should be considered within the scope of the invention as well.

Figure 3:
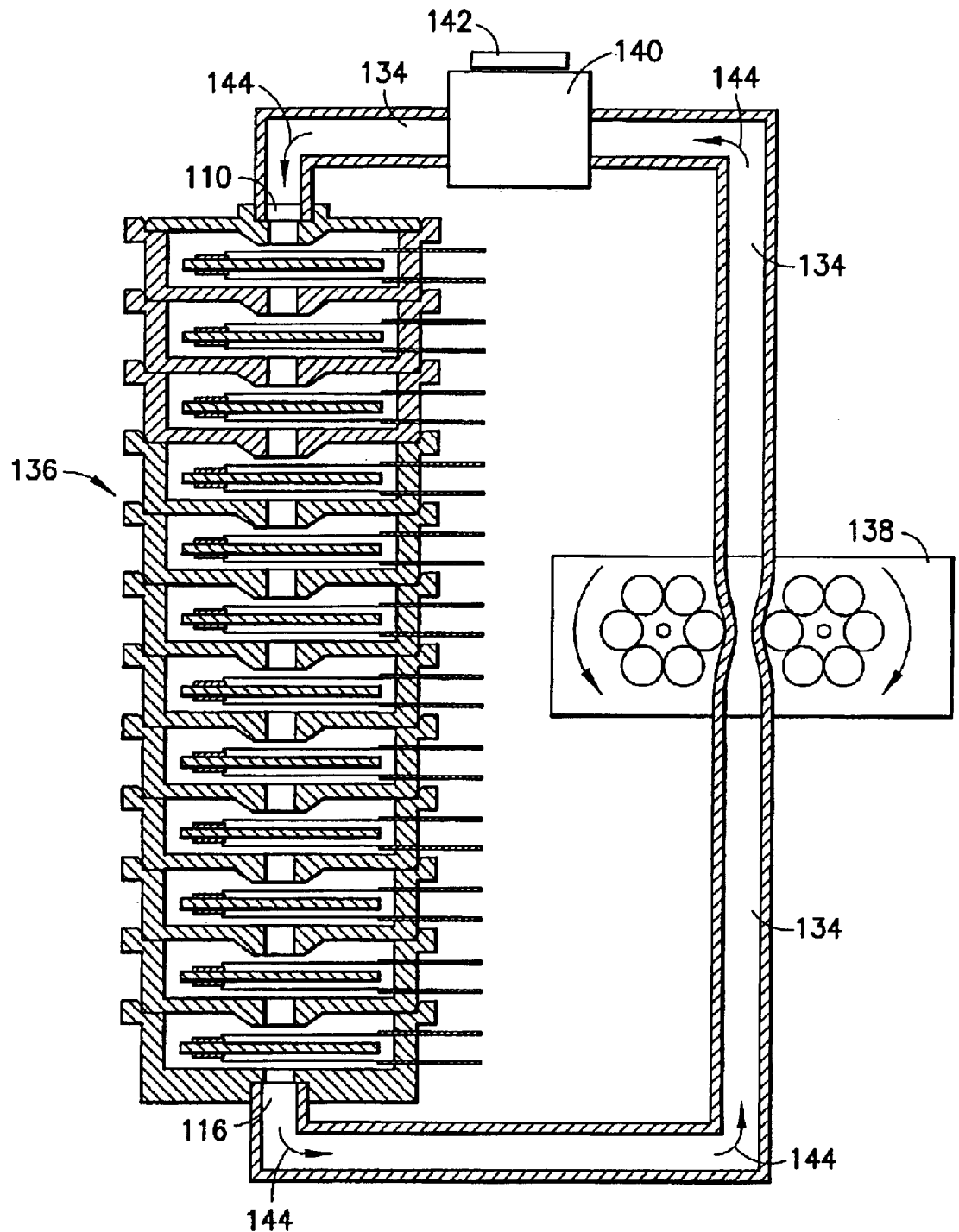
FIG. 3 shows a stack of base units and a pump, whereby the liquid sample is entered into the detection device through a fill and vent unit, and is re-circulated through the stack of base units by means of a peristaltic pump and a loop of flexible tubing.

No matter if one base unit 105 is used, or if a number of base units 105 is connected together to build a stack of such units as shown in FIG. 2, the liquid sample is guided into the unit(s) via tubing 134, which is illustrated in FIG. 3. A closed loop of such tubing 134 is provided to allow for continuous re-circulation of sample fluid through the unit(s) 136. The fluid circulation is preferably achieved by utilizing flexible tubing, and by mounting a peristaltic pump 138 onto the closed tubing loop. A fill-and-vent unit 140 with a removable lid 142 allows bringing the liquid sample into the system. As indicated by arrows 144 in FIG. 3, the liquid sample enters the stack of base units at flange 110. After passing through all units, the liquid sample leaves the stack of units at flange 116, passes peristaltic pump 138, and reenters the stack of units again at flange 110.

Figure 4:
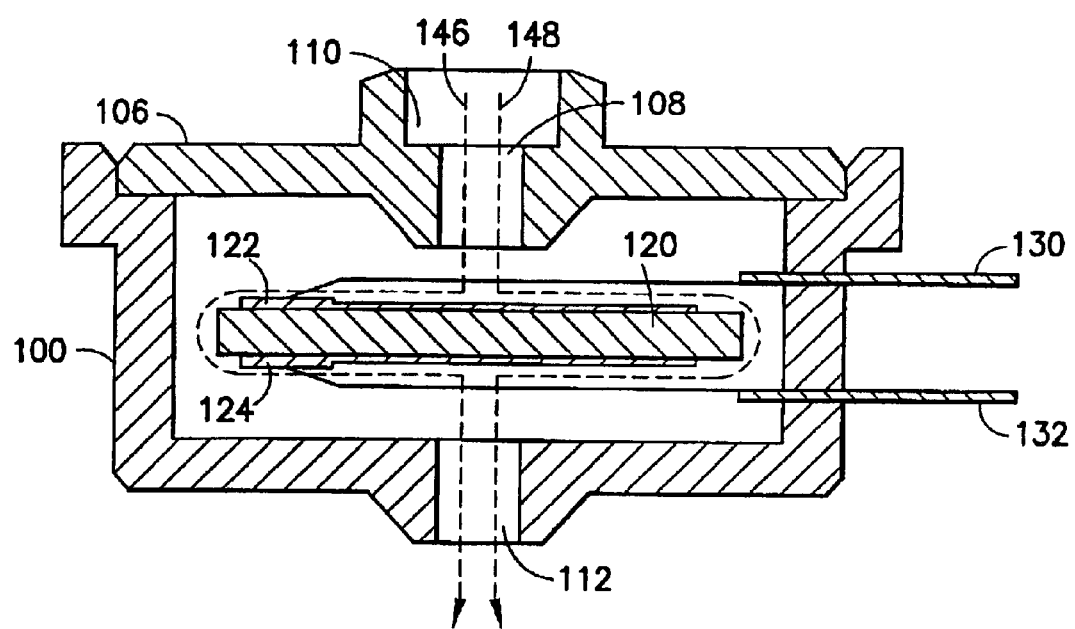
FIG. 4 illustrates the sample flow within a base unit that provides maximum contact of target molecules with the sensing surface according to an embodiment of the present invention.

Due to the narrow entrance at through hole 108 and exit 112 of the base unit as shown in FIG. 4, the liquid sample containing the target molecules in low concentration is guided across the sensing surface or surfaces of crystal(s) 120, which is indicated by arrows 146 and 148. This more readily brings the few target molecules in close proximity to the sensing surface, resulting in more efficient specific binding during the continuous re-circulation of the liquid sample. Therefore, no pre-concentration step such as centrifugation is required.

Figure 5:
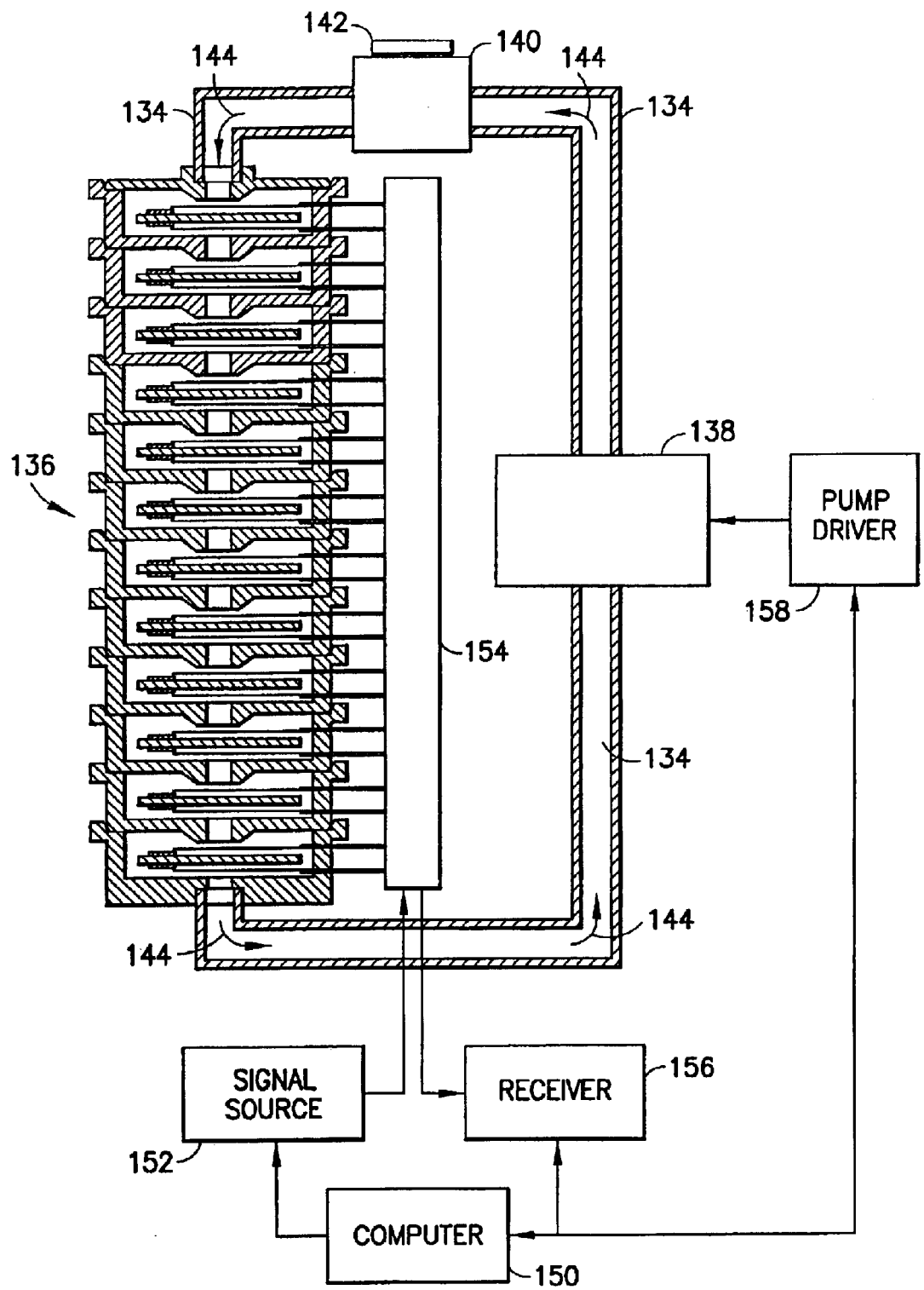
FIG. 5 illustrates schematically a complete apparatus according to an embodiment of the present invention, whereby the sensing surfaces within the base units are electro-acoustically interrogated according to an embodiment of the present invention.

FIG. 5 illustrates schematically a complete apparatus according to the present invention, whereby the sensing surfaces within the stack of base units 136 are interrogated by applying principles of electro-acoustics.

The liquid sample containing the target molecules of interest in low concentration is introduced into the apparatus at fill-and-vent unit 140, which has a removable lid 142. A closed loop of tubing 134 connects fill-and-vent unit 140 with the stack of units 136, and with a peristaltic pump 138. Preferably, tubing 134 is made out of flexible material. A computer 150 is connected with an electronic signal source 152, which is in turn connected with a connector and directional coupler 154 at the feed-throughs described and/or shown in FIGS. 1 to 4. Connector and directional coupler 154 guides an RF signal from signal source 152 towards piezo-acoustic crystals 120 within the stack of units 136. Connector and directional coupler 154 is also connected with the input of an RF receiver 156, and the output of RF receiver 156 is connected to computer 150. Finally, computer 150 is connected to a pump driver 158 that in turn is connected to peristaltic pump 138. Arrows 144 in FIG. 5 show how the liquid sample circulates within tubing 134.

In operation, after the liquid sample has been introduced into the system, computer 150 triggers pump driver 158 and, consequently, peristaltic pump 138. Due to this action, the liquid sample starts circulating within the system and, as shown in FIG. 4, passes the sensing surfaces of piezo-electric crystals 120 within stack 136 in close proximity, which enhances the probability for specific binding on said surfaces. Preferably, computer 150 and pump driver 158 are programmed to periodically reverse the flow or liquid to further enhance binding efficiency and to reduce dead-zones in the liquid, such as might develop in corners of housing 100. After a predetermined incubation time period (e.g. 30 minutes) computer 150 activates signal source 152, which results in an oscillation of said sensing surfaces on crystals 120.

If binding events have taken place during said incubation time period, target molecules will break away from said sensing surfaces due to the surfaces' oscillation, which results in an acousto-electric signal that is being detected by RF receiver 156.

Figure 6:
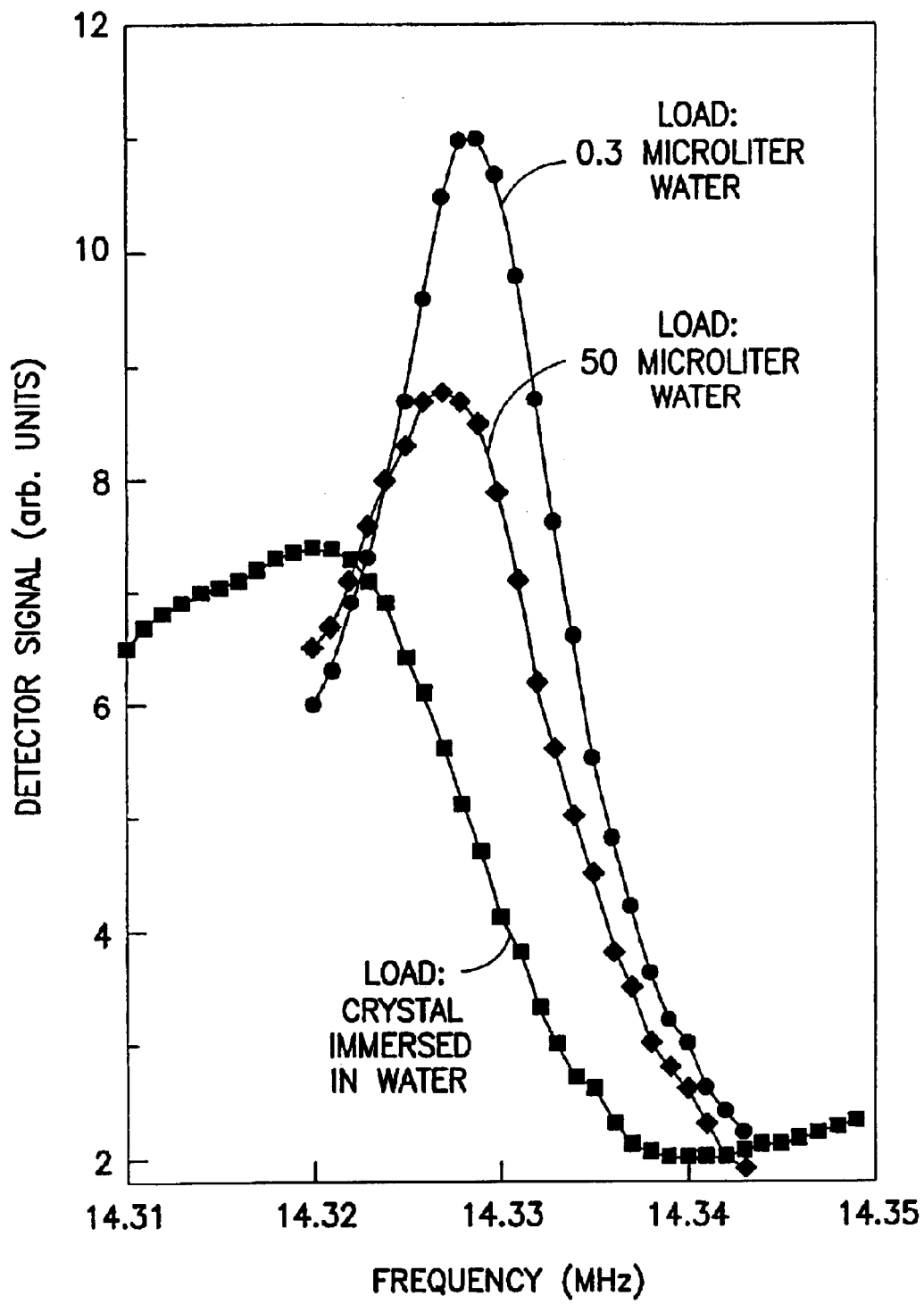
FIG. 6 shows experimental results illustrating the resonance spectrum of a 14.3-MHz piezo-electric quartz crystal under increasing liquid loading conditions.

FIG. 6 shows experimental results illustrating the resonance spectrum of a 14.3-MHz piezo-acoustic quartz crystal under increasing liquid loading conditions. FIG. 6 illustrates the fact that if only a small percentage of the sensing surface comes into contact with the liquid sample (0.3 microliter water load), then the resonance curve is very narrow. If the crystal is completely immersed in liquid, as is the case in an apparatus according to the present invention, then the resonance curve becomes wider, but it is still narrow enough to allow for acousto-electric detection of binding events.

Figure 7A:
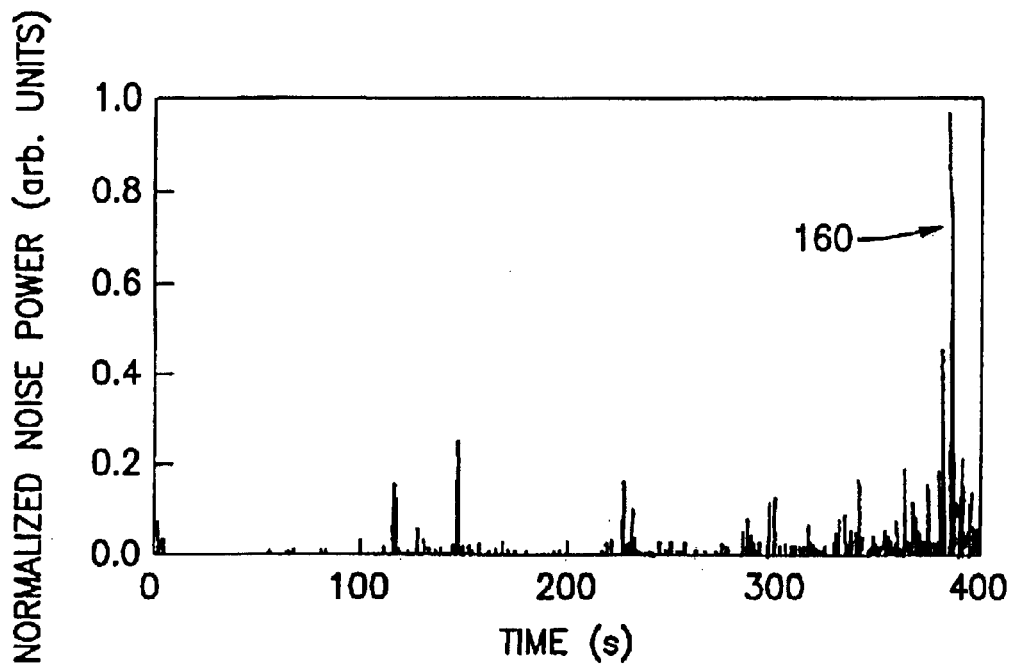
FIG. 7(a) illustrates experimental data in the form of acoustic spectra with plastic PMMA beads attached to the piezo-electric quartz crystal.
Figure 7B:
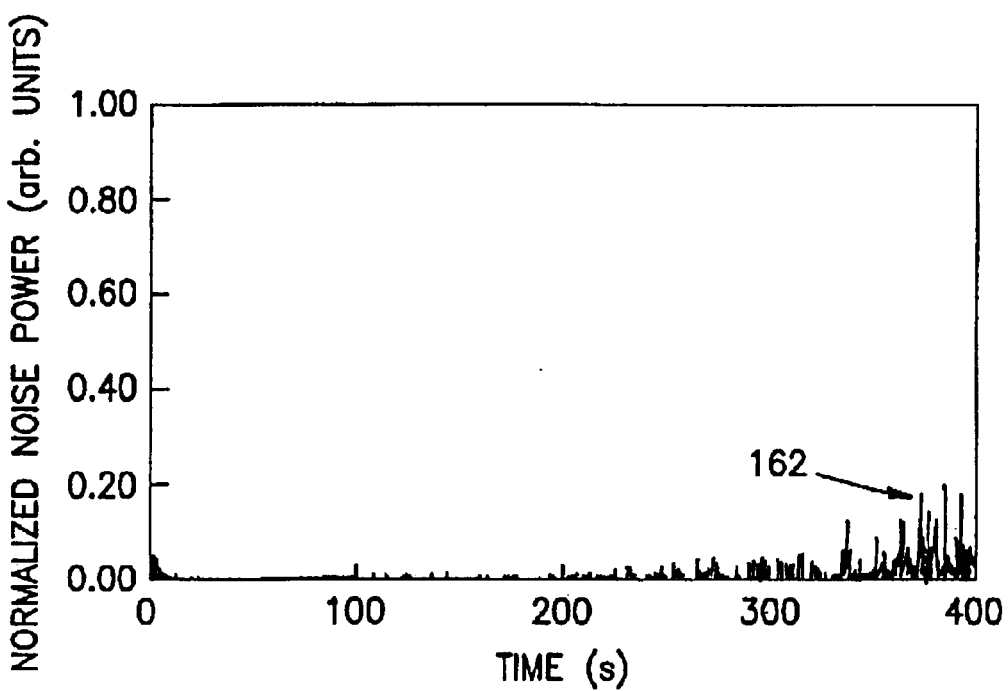
FIG. 7(b) illustrates experimental data in the form of acoustic spectra with no beads attached.

FIG. 7(a) illustrates experimental data in the form of acoustic spectra with plastic PMMA beads attached to the above-mentioned piezo-acoustic quartz crystal. FIG. 7(b) illustrates experimental data in the form of acoustic spectra with no beads attached. As illustrated in FIG. 7(a), if targets such as small beads had been bound to the sensing surface, peaks 160 with amplitudes larger than noise peaks are observed. FIG. 7(b) illustrates lower amplitude noise peaks 162.

In an apparatus according to the present invention, the stack of base units 136 may comprise base units having identical sensing surfaces, or may comprise base units having sensing surfaces that have been activated for the binding of different target molecules on different crystals. Including sensing surfaces activated for binding to different target molecules achieves multiplexed analyte detection. Including identical sensing surfaces in the stack 136 results in an increased overall size of sensing surface, and, consequently, in an improved detection limit for low analyte concentration.

The base units for an apparatus according to an embodiment of the present invention are easily manufactured, and advantageously can be produced in large numbers at low cost. The sensing surfaces are easily prepared for single base units, before more than one base unit are connected together. Due to the open flange design, before connecting them, the interior of a base unit is readily accessible, which also makes the mounting of crystals 120 very easy. After preparing groups of base units, where each group has been activated for a particular target molecule of interest, members from multiple groups can be connected together to form stacks of base units 136 that represent specific multi-analyte assays.

The re-circulation of the sample liquid can be performed over an extended incubation time period to allow for binding of all target molecules that are present within the sample volume. It is possible and advantageous to reverse the flow direction for the liquid sample periodically to avoid trapping of target molecules in corners or other dead zones of the base units.

In a modification of the invention, the fill-and-vent unit 140 shown in FIGS. 3 and 5 can become part of lid 106 in a top unit 107 shown in FIGS. 1 to 4.

A typical electro-acoustic crystal 120 according to a preferred embodiment of the invention has the shape of a disc with a thickness of approximately 0.1 mm, and a diameter between 5 and 10 mm. Based on this, the volume of a base unit can be as low as 100 microliters. This would result in an overall sample volume around 1 ml for a stacked detection device 136 containing ten base units.

The closed loop tubing 134 is preferably made out of a flexible plastic material, but of course it will be readily understood by those of skill in the art that a stiff tubing material or any other suitable material could be used without departing from the spirit of the invention. Those of skill in the art will also recognize that peristaltic pump 138 can be replaced with any other kind of suitable pumping device.

It will be appreciated that an apparatus according to the present invention is not limited to the use of piezo-acoustic crystals. It would still be within the scope of the invention to use piezo-acoustic plastic materials, piezo-acoustic foils, piezo-acoustic microstructures on solid substrates, or the like.

While the invention herein disclosed has been described by means of specific embodiments and applications thereof, numerous modifications and variations can be made thereto by those skilled in the art without departing from the scope of the invention as set forth in the claims.

What is claimed is:

1. A liquid sample sensing device comprising a top unit, at least one base unit, and a bottom unit arranged in a stack, each base unit comprising:

a volume defined by at least one side wall, a top flange member, and a bottom member having disposed therein at least one sensing body comprising a respective surface that is activated for binding to target molecules, said sensing body having attached thereto at least two electrodes, said electrodes extending outside said volume, said top flange member adapted to engage a bottom member of an adjacent base unit such that said stack is substantially sealed, said device filter comprising a pump having a loop of tubing connected to a top of said top unit and a bottom of said bottom unit to form a closed loop.

2. The liquid sample sensing device of claim 1, wherein said pump is a peristaltic pump.

3. The liquid sample sensing device of clam 1, wherein a plurality of said sensing body surfaces are activated for binding to the same type of target molecule.

4. The liquid sample sensing device of claim 1, wherein a plurality of said sensing body surfaces are each activated for binding to a different type of target molecule.

5. The liquid sample sensing device of claim 1, wherein each base unit top flange member is adapted to engage a bottom member of an adjacent base unit or top unit.

6. The liquid sample sensing device of claim 1, wherein each base unit bottom member is adapted to engage a top flange member of an adjacent base unit or bottom unit.

7. The liquid sample sensing device of claim 1, wherein said bottom member comprises a liquid exit opening adapted to allow liquid to flow out of said volume and into one of a next base unit and said bottom unit.

8. The liquid sample sensing device of claim 7, wherein said exit opening is narrow relative to a surface area of said sensing body, and wherein said exit opening is located substantially adjacent to said surface to cause a liquid sample flowing through said volume to flow over a substantial portion of said surface.

9. The liquid sample sensing device of claim 1, wherein said sensing body is an electroacoustic body.

10. The liquid sample sensing device of claim 9, wherein said sensing body is a piezoelectric crystal.

11. A method of sensing target molecules within a liquid sample comprising:

providing a top unit, at least one base unit, and a bottom unit, each base unit comprising a volume defined by at least one side wall, a top flange member, and a bottom member having disposed therein at least one sensing body, each of said sensing bodies having attached thereto at least two electrodes, said electrodes extending outside said volume, said bottom member comprising an opening substantially adjacent to said sensing body to allow fluid to flow from said volume into said adjacent unit or said bottom unit, said top flange member adapted to engage a bottom member of a top flange unit of an adjacent base unit or a bottom unit to form a substantially sealed volume in said adjacent unit or bottom unit, stacking said top unit, at least one base unit, and bottom unit to form a stack;

attaching a pump and a closed loop of tubing to said top unit and said bottom unit;

pumping sample fluid through said stack for a predetermined incubation tine period;

exciting at least one of said sensing bodies through said respective electrodes; and measuring electrical signals generated by said sensing body at said electrodes.

12. The method of claim 11, wherein said tubing is flexible tubing, and said pump is a peristaltic pump.

13. The method of claim 11, wherein each said sensing body comprises a surface that is activated for binding to target molecules.

14. The method of claim 13, wherein a plurality of said sensing body surfaces are activated for binding to the same type of target molecule.

15. The method of claim 13, wherein a plurality of said sensing body surfaces ace each activated for binding to a different type of target molecule.

16. The method of claim 11, wherein at least one of said sensing bodies comprises and electroacoustic body.

17. The method of claim 16, wherein said electroacoustic body comprises a piezoelectric cal.

18. The method of claim 11, wherein said pumping step further comprises periodically reversing the flow of said sample fluid.

19. A liquid sample sensing device comprising:

a stack of at least one stackable base units, whereby each of said at least one base units comprises
   (a) a sidewall and a bottom member defining an interior space, with the bottom member adapted to connect to the sidewall of an adjacent base unit in said stack:
   (b) at least one body mounted inside said interior space, each said bode containing at least one sensing surface: and
   (c) a through hole in said bottom member allowing for fluid communication with the adjacent base unit in said stack, and adapted to direct liquid sample flow onto the at least one sensing surface of said body in the adjacent base unit;

a lid attached to said sidewalls of a to; base unit, said lid having an entrance hole adapted for receiving the exit conduit of a sample re-circulation loop;

wherein said through hole of a bottom base unit comprises an exit hole adapted for receiving the entrance conduit of said sample re-circulation loop: and wherein said at least one body is an electroacoustic member.

20. A liquid sample sensing device comprising:

a stack of at least one stackable base units, whereby each of said at least one base units comprises
   (a) a sidewall and a bottom member defining a interior space, with the bottom member adapted to connect to the sidewall of an adjacent base unit in said stack;
   (b) at least one body mounted inside said interior space, each said containing at least one sensing surface; and
   (c) a though hole in said bottom member allowing for fluid communication with the adjacent base unit in said stack and adapted to direct liquid sample flow onto the at last one sensing surface of said body in the adjacent base unit;

a lid attached to said sidewalls of a top base unit, said lid having an entrance hole adapted for receiving the exit conduit of a sample re-circulation loop;

wherein said through hole of a bottom base unit comprises an exit hole adapted for receiving the entrance conduit of said sample re-circulation loop; and wherein said at least one body is adapted to generate a sensor output signal based on changes in the bodies' electrical conductivity.

21. A liquid sample sensing device comprising:

a stack of at least one stackable base units, whereby each of said at least one base units comprises
   (a) a sidewall and a bottom member defining an interior space, with the bottom member adapted to connect to the sidewall of an adjacent base unit in said stack:
   (b) at least one body mounted inside said interior space, each said body containing at least one sensing surface; and
   (c) a through hole in said bottom member allowing for fluid communication with the adjacent base unit in said stack, and adapted to direct liquid sample flow onto the at least one sensing surface of said body in the adjacent base unit;

a lid attached to said sidewalls of a top base unit said lid having an entrance hole adapted for receiving the exit conduit of a sample recirculation loop;

wherein said through hole of a bottom base unit comprises an exit hole adapted for receiving the entrance conduit of said sample re-circulation loop; and wherein said at least one body is an electro-chemical sensing body.

22. A liquid sample sensing device comprising:

a stack of at least one stackable base units, whereby each of said at least one base units comprises
   (a) a sidewall and a bottom member defining an interior space, with the bottom member adapted to connect to the sidewall of an adjacent base unit in said stack;
   (b) at least one body mounted inside said interiors, each said body containing at least one sensing surface; and
   (c) a through hole in said bottom member allowing for fluid communication with the adjacent base unit in said stack, and adapted to direct liquid sample flow onto the at least one sensing surface of said body in the adjacent base unit;

a lid attached to said sidewalls of a top base unit said lid having an entrance hole adapted for receiving the exit conduit of a sample re-circulation loop;

wherein said through hole of a bottom base unit comprises an exit hole adapted for receiving the entrance conduit of said sample re-circulation loop; and further comprising electrodes connected to said body and extending outside of said interior space.

* * * * *